United States Patent [19]
Shturman et al.

[11] Patent Number: 5,779,722
[45] Date of Patent: Jul. 14, 1998

[54] ATHERECTOMY DEVICE HANDLE WITH GUIDE WIRE CLAMP OVERRIDE DEVICE

[75] Inventors: Leonid Shturman, Minnetonka, Minn.; Georgiy Morov, Moscow, Russian Federation

[73] Assignee: Shturman Cardiology Systems, Inc., Minneapolis, Minn.

[21] Appl. No.: 792,101

[22] Filed: Jan. 31, 1997

Related U.S. Application Data

[63] Continuation-in-part of Ser. No. 785,991, Jan. 21, 1997.
[51] Int. Cl.⁶ .................................................. A61B 17/22
[52] U.S. Cl. .................................... 606/159; 606/180
[58] Field of Search .............................. 606/1, 80, 159, 606/167, 170, 171, 180

[56] References Cited

U.S. PATENT DOCUMENTS

| 4,990,134 | 2/1991 | Auth | 604/22 |
|---|---|---|---|
| 5,314,407 | 5/1994 | Auth et al. | 604/22 |
| 5,314,438 | 5/1994 | Shturman | 606/159 |
| 5,490,859 | 2/1996 | Mische et al. | 606/159 |
| 5,681,336 | 10/1997 | Clement et al. | 606/159 |

*Primary Examiner*—Glenn K. Dawson
*Attorney, Agent, or Firm*—Fredrikson & Byron, P.A.

[57] ABSTRACT

An atherectomy device having a handle housing, a rotatable prime mover movable longitudinally with respect to the handle housing, a rotatable drive shaft having a proximal end connected to the prime mover for rotation and longitudinal movement therewith, and a distal end portion having a tissue removal implement usable to remove tissue from a bodily passageway. A guide wire clamp is disposed within the handle housing for releasably clamping the proximal portion of a guide wire. An override clamp is removably securable to the handle housing for moving the guide wire clamp to a guide wire-released position and for holding the guide wire clamp in such released position. The override clamp may also include a mechanical linkage to the prime mover so that the override clamp locks the prime mover in a particular longitudinal position with respect to the handle housing.

22 Claims, 14 Drawing Sheets

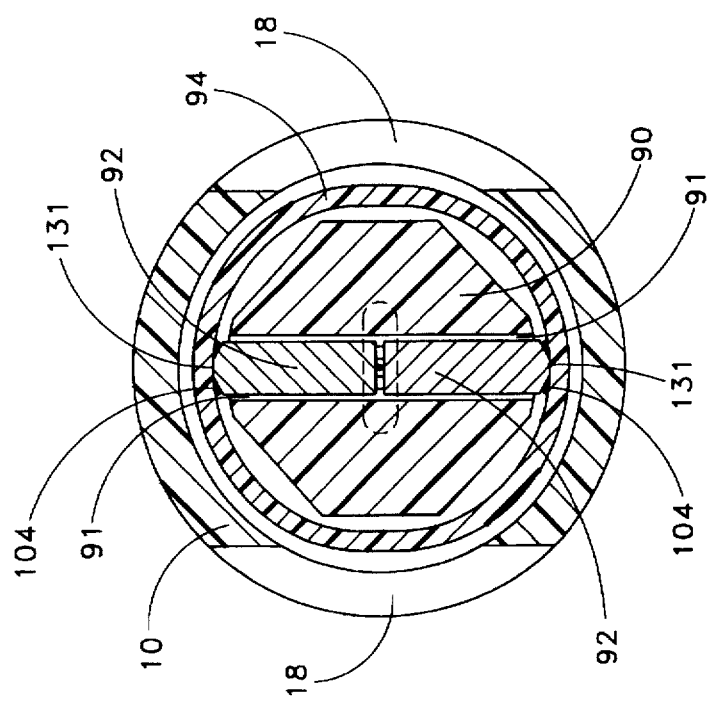
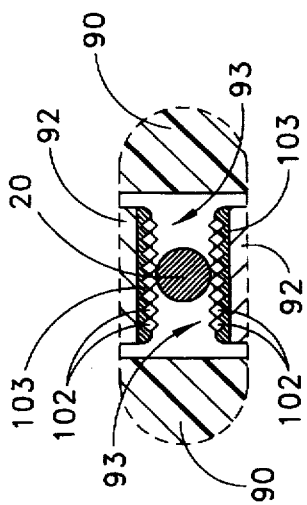
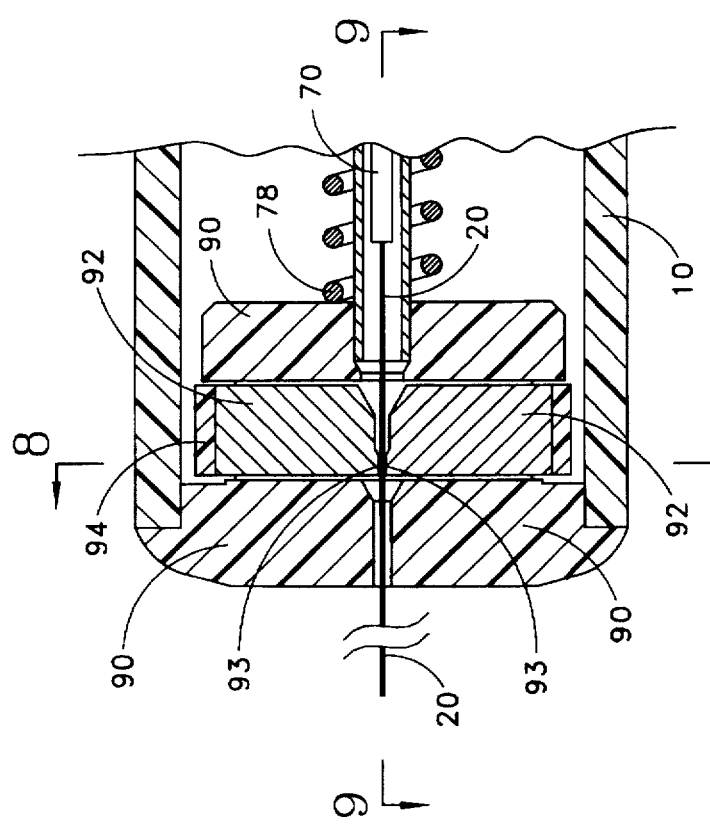
FIG. 8
FIG. 8A
FIG. 7

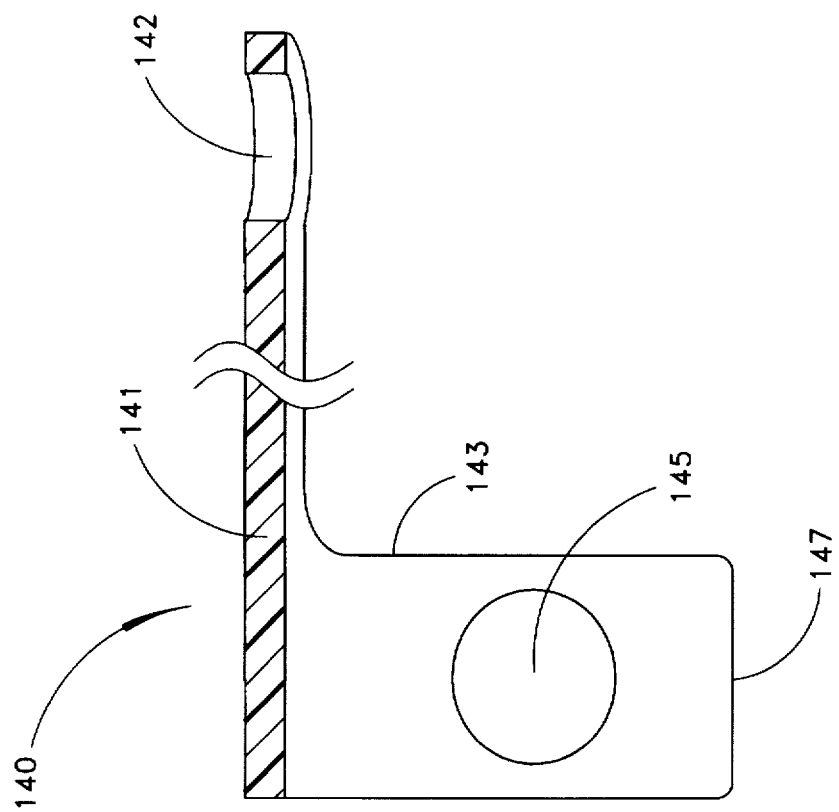
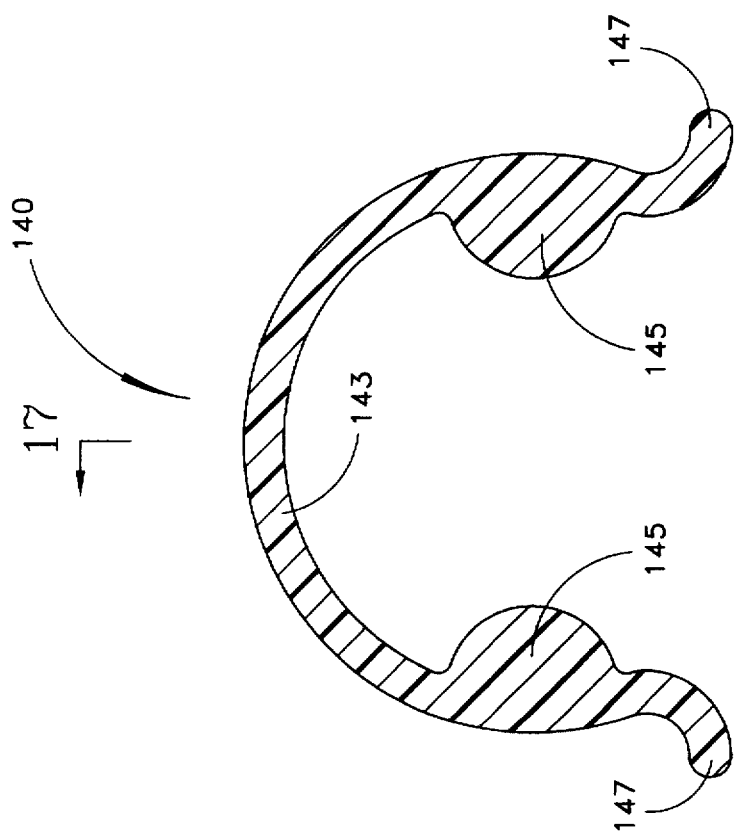
FIG. 17
FIG. 16

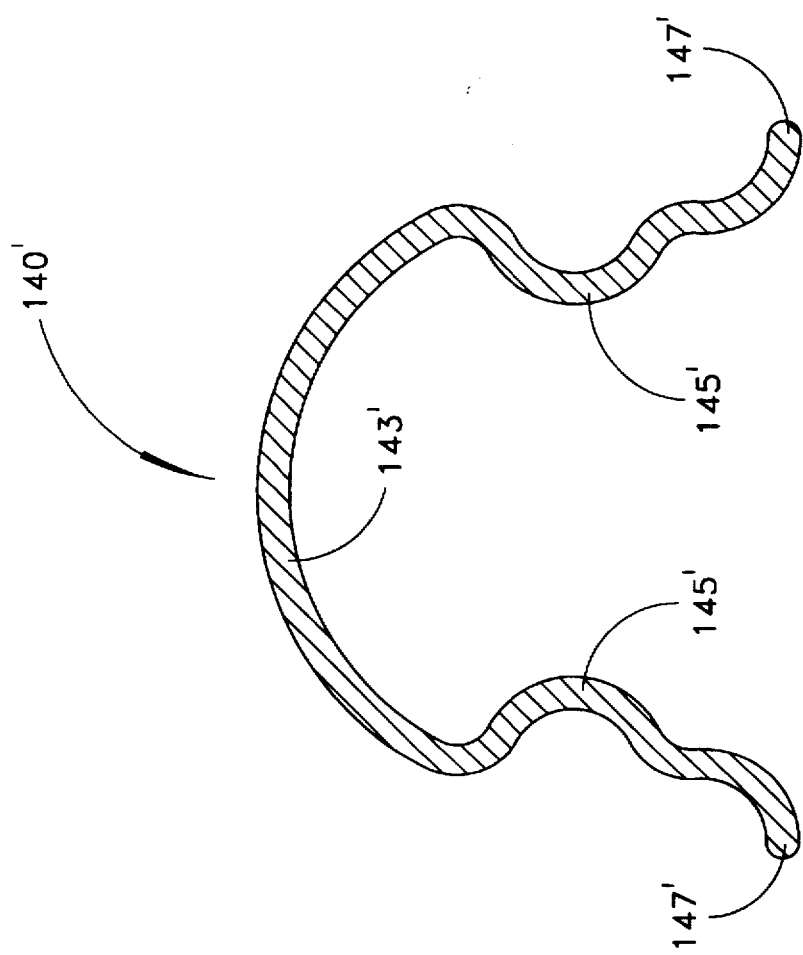

ATHERECTOMY DEVICE HANDLE WITH GUIDE WIRE CLAMP OVERRIDE DEVICE

CROSS REFERENCE TO RELATED APPLICATION

This application is a continuation in part of a co-pending application filed on Jan. 21, 1997, Ser. No. 08/785,991, naming the same inventors, entitled "Handle for Atherectomy Device."

TECHNICAL FIELD

The invention relates to devices utilized in removing tissue from body passageways, such as removal of atherosclerotic plaque from arteries, utilizing a rotational atherectomy device. In particular, the invention relates to improvements in a handle for a rotational atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (Auth), a rotating burr covered with an abrasive cutting material, such as diamond grit (diamond particles or dust), is carried at the distal end of a flexible, rotatable drive shaft.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

U.S. Pat. No. 5,314,407 (Auth) shows details of a type of handle which may be used in conjunction with rotational atherectomy devices of the type shown in the Auth '134 and Shturman '438 patents. A handle of the type shown in the Auth '407 patent has been commercialized by Heart Technology, Inc. (Redmond, Wash.), now owned by Boston Scientific Corporation (Natick, Mass.) in the rotational atherectomy device sold under the trademark Rotablator®.

The Rotablator® device is depicted in FIG. 1. It includes a compressed gas driven turbine located inside a handle housing A. The compressed gas driven turbine is connected to a drive shaft B having an abrasive coated burr C at its distal end. The drive shaft and the burr are rotated at high speeds, typically in the range of, e.g., about 150,000 to about 190,000 rpms. The drive shaft is designed to be advanced over and rotated around a guide wire D. For most of its length the drive shaft is disposed inside a catheter E. A pair of legs L are secured to the bottom of the generally cylindrical handle housing A.

The turbine of the Rotablator® device is carried in a turbine carriage J which is movable longitudinally within the handle housing A. The proximal end of the drive shaft B is secured to the turbine, so that longitudinal movement of the turbine carriage permits advancement and retraction of the abrasive coated burr C over the guide wire D. To facilitate movement of the turbine carriage forward and backward a control knob K is provided, the control knob K being secured to the turbine carriage J by a shaft that extends outwardly through a slot in the handle housing A.

A pneumatic guide wire clamp is built into the proximal end portion of the handle housing A to prevent the guide wire D from rotating when the turbine and drive shaft B are rotated. Compressed gas is supplied to the pneumatic guide wire clamp by a flexible gas supply tube F. This gas supply tube F is connected to a rigid conduit that extends through the handle housing A and is connected to a flexible U-shaped tube G which supplies compressed gas to the turbine.

An override mechanism is provided to permit the user to release the guide wire clamp even when the compressed gas is supplied to the Rotablator® atherectomy device and the drive shaft is rotating. This override mechanism is activated by pressing on the override button H. Although normally the guide wire D should be clamped when the turbine is rotating (to prevent the guide wire D from rotating along with the drive shaft B), under certain circumstances it is desirable to unclamp the guide wire D when the drive shaft B is rotating.

For example, after the guide wire D has been properly advanced into the patient's artery and across the stenosis to be treated, the drive shaft B with its abrasive coated burr C is advanced over the guide wire D. It has been found that advancement of the drive shaft B over the guide wire D can be accomplished quite easily if the drive shaft B is rotated at a relatively low speed (e.g., from about 50,000 to about 90,000 rpm). The operator can accomplish this by firmly holding any conventional guide wire clip applied to the guide wire D (proximally of the handle housing A) and pressing on the override button H (releasing the guide wire D from the clamp in the handle housing A) while advancing the drive shaft B and the handle housing A over the guide wire. The same technique (i.e., rotating the drive shaft at a relatively low speed) may be used to withdraw the atherectomy device over the guide wire from the patient's body at the end of the procedure. Sometimes during the atherectomy procedure there also may be a need to advance the guide wire while the drive shaft is rotating. Such technique also requires the operator to hold and manipulate the guide wire using the conventional guide wire clip while depressed the override button H.

To prevent the override mechanism from inadvertently being left in the unclamped position, the override button H of the Rotablator® device is spring loaded, so that constant pressure must be exerted to keep it depressed. This requires the user (or an assistant) to constantly hold the override button H until the drive shaft is entirely advanced over the guide wire D to its desired position within the patient's artery. It would be desirable, therefore, to provide a guide wire clamp override mechanism which could be activated safely without continuously occupying one of the operator's hands (or one of the assistant's hands).

SUMMARY OF THE INVENTION

The invention provides an atherectomy device having a handle housing, a rotatable prime mover movable longitudinally with respect to the handle housing, a rotatable drive shaft having a proximal end connected to the prime mover for rotation and longitudinal movement therewith, and a distal end portion having a tissue removal implement usable to remove tissue from a bodily passageway. A guide wire is disposed within the drive shaft and has a proximal portion extending proximally from the proximal end of the drive shaft. A guide wire clamp is disposed within the handle housing for releasably clamping the proximal portion of the guide wire, the guide wire clamp being selectively movable from a guide wire-clamped position to a guide wire-released position. The handle housing is shaped and sized with respect to the guide wire clamp to permit manual movement of the guide wire clamp from its guide wire-clamped position to its guide wire-released position. The atherectomy device handle of the invention is provided with an override clamp which is removably securable to the handle housing and usable for moving the guide wire clamp to the guide wire-released position and for holding the guide wire clamp in such position. The override clamp allows the guide wire clamp to be moved to its guide wire-released position safely and reliably without continuously occupying one of the operator's hands (or one of the assistant's hands).

Preferably the override clamp includes a generally C-shaped portion with a pair of inwardly protruding curved buttons for operative engagement with the clamp biasing mechanism to move the guide wire clamp to its guide wire-released position.

In a preferred embodiment the atherectomy device includes a prime mover connected to a control knob external to the handle housing. The prime mover, located within the handle housing, preferably is connected to the control knob by a shaft extending through a longitudinal slot in the handle housing. The control knob facilitates longitudinal movement of the prime mover and the drive shaft with respect to the handle housing. In the preferred embodiment it is possible to use the override clamp not only to move the guide wire clamp into its guide-wire released position, but also to lock the control knob in a particular longitudinal position with respect to the handle housing. This can be accomplished by providing the override clamp with a mechanical linkage engagable with the control knob. Preferably the mechanical linkage comprises a strap extending distally from the generally C-shaped portion of the override clamp, and preferably the strap has, at its distal end, an orifice sized and shaped to closely receive and retain the control knob.

BRIEF DESCRIPTION OF THE DRAWINGS

FIG. 7 is a longitudinal cross-sectional view of the clamp portion of the atherectomy device of the invention;

FIG. 8 is a transverse cross-sectional view of FIG. 7, taken along lines 8—8 thereof;

FIG. 8A is an enlarged view of a portion of FIG. 8;

FIG. 16 is a transverse cross-sectional view of the override clamp of the invention;

FIG. 17 is a longitudinal cross-sectional view of the override clamp of FIG. 16, taken along lines 17—17 thereof; and FIG. 18 is a transverse cross-sectional view of an alternate embodiment of an override clamp of the invention.

DETAILED DESCRIPTION OF THE INVENTION

Figure 1:
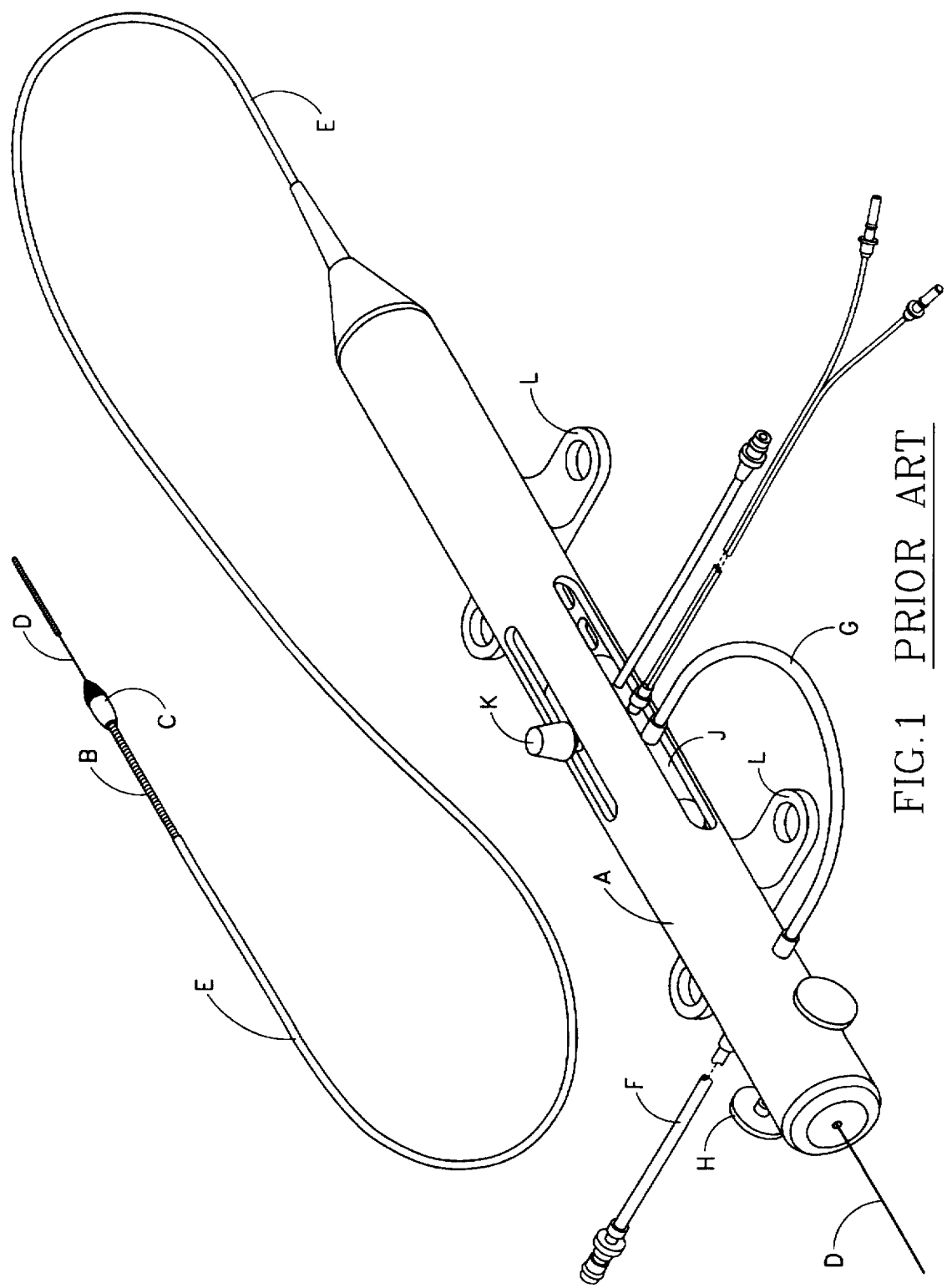
FIG. 1 is a perspective view of the prior art Rotablator® rotational atherectomy device described above.
Figure 2:
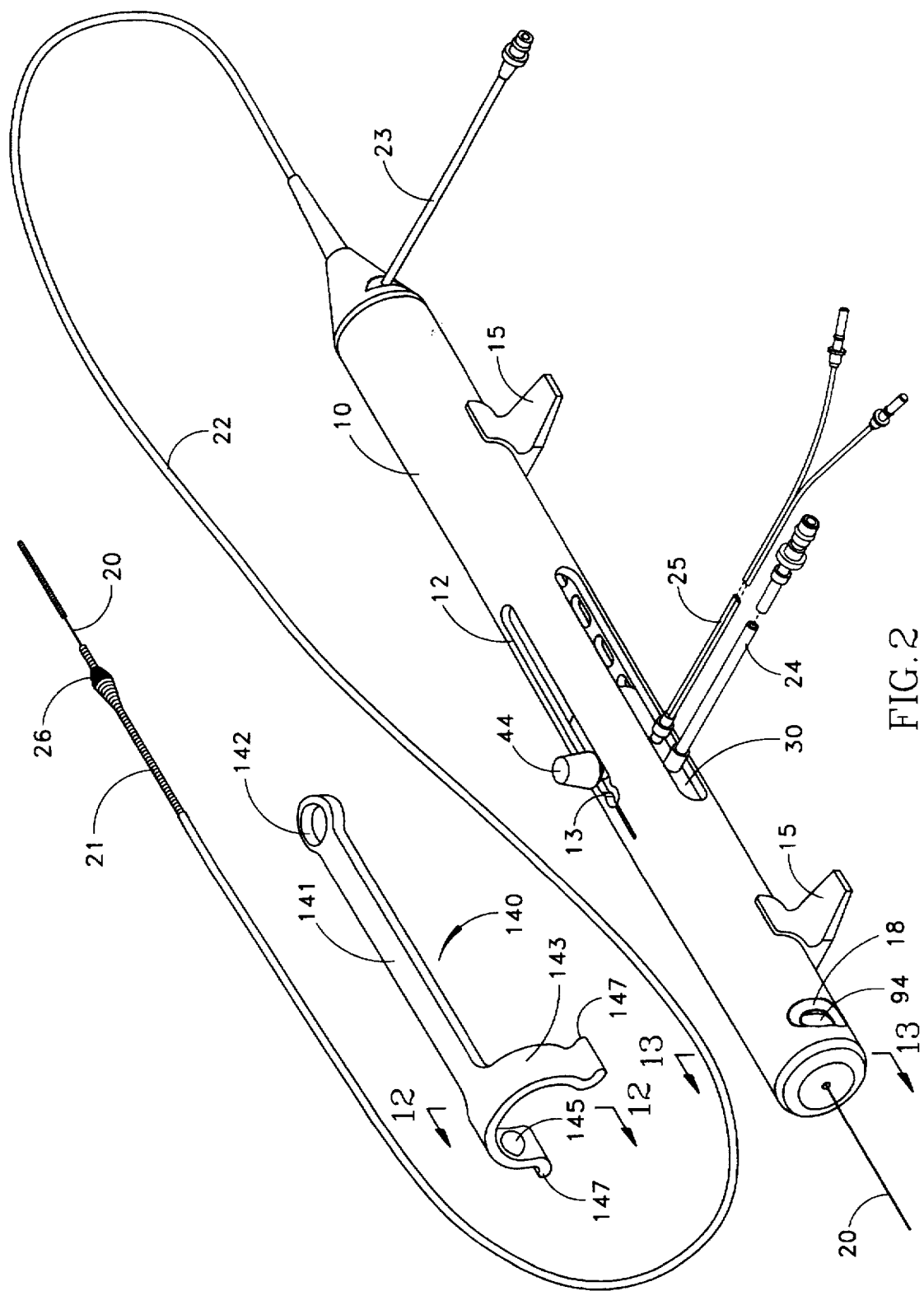
FIG. 2 is a perspective view of a rotational atherectomy device of the invention with the override clamp detached from the handle housing.

FIG. 2 illustrates in perspective view an atherectomy device of the invention. While a full description of the device for purposes of understanding the present invention follows, additional details regarding the operation and function of the atherectomy device are contained in a co-pending application filed by the same inventors as the present application on Jan. 21, 1997, Ser. No. 08/785,991, entitled Handle for Atherectomy Device, incorporated herein by reference. The device includes a handle having a housing 10, an elongated, flexible drive shaft 21 (typically constructed from multifilar helically coiled wire) having a tissue removal section 26 near its distal end, and an elongated catheter 22 extending distally from the handle housing 10. The catheter 22 has a lumen in which most of the length of the drive shaft 21 is disposed, the tissue removal section 26 extending distally beyond the distal end of the catheter 22. The drive shaft 21 also contains an inner lumen, permitting the drive shaft 21 to be advanced over a guide wire 20, which desirably extends both proximally of the handle housing 10 and distally beyond the drive shaft 21. A fluid supply line 23 may be provided for introducing a cooling and lubricating solution (typically saline or another biocompatible fluid) into the catheter 22.

A rotatable prime mover (such as a compressed gas driven turbine or similar supply of rotational motion) is connected to the proximal end of the drive shaft 21. In the preferred embodiment illustrated in the drawings the prime mover is disposed within the handle housing 10, and it is carried by a prime mover carriage 30 (sometimes referred to as a turbine carriage) which can be moved longitudinally within the handle housing 10 through a limited range of motion. A control knob 44 (secured to the prime mover carriage 30) is provided to facilitate advancing and retracting of the prime mover and rotatable drive shaft 21 with respect to the catheter 22 and the handle housing 10.

Preferably the prime mover is a turbine powered by compressed gas such as compressed nitrogen or compressed air. For this purpose a compressed gas supply line 24 may be provided, the supply line being connected to the turbine carriage 30. A pair of fiber optic cables 25 may also be provided for monitoring the speed of rotation of the turbine and drive shaft 21 (e.g., as described in the Auth '407 patent and implemented in the Rotablator® device). A pair of legs 15 attached to the handle housing 10 is also provided. For the sake of clarity, the legs 15 are not illustrated in some of the drawings.

Figure 3:
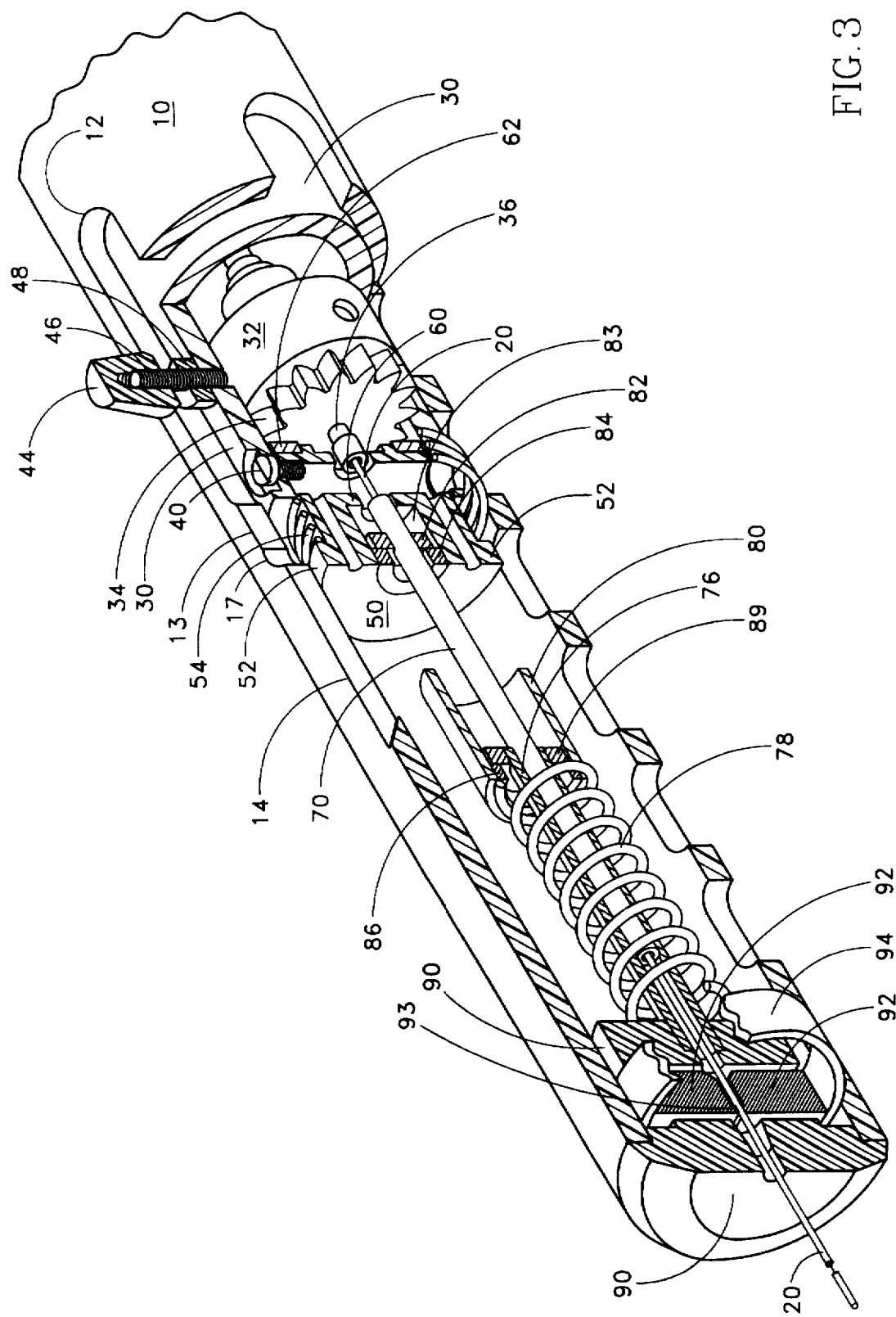
FIG. 3 is a perspective view of the proximal portion of the handle of the atherectomy device of FIG. 2, shown in partial longitudinal cross-section.
Figure 4:
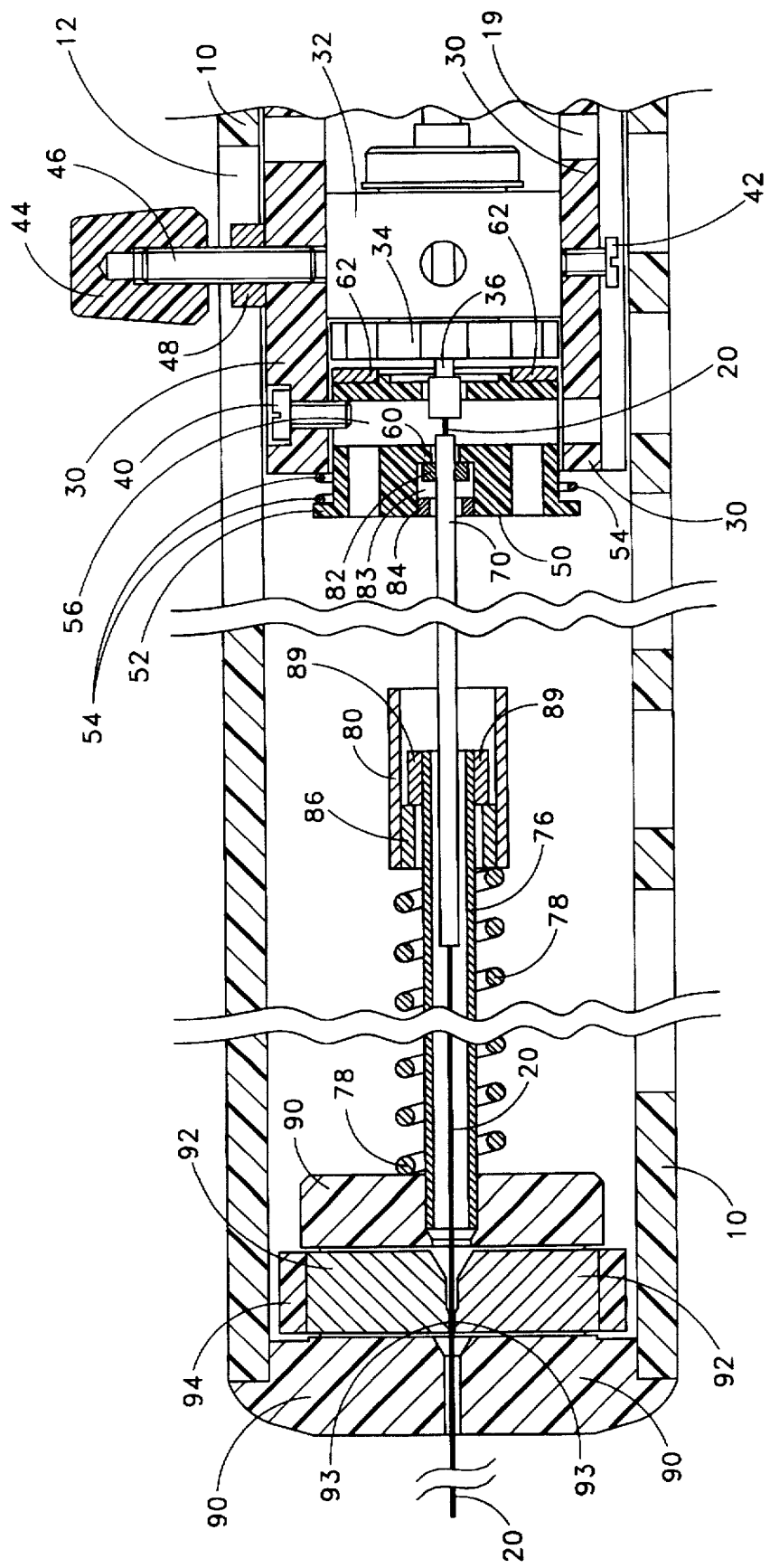
FIG. 4 is a longitudinal cross-sectional view of the proximal portion of the handle of the device of FIG. 2, the turbine carriage being located in a slightly moved position.

FIG. 3 provides a broken-away perspective view of the internal components of one embodiment of the atherectomy device handle of the invention, and FIG. 4 illustrates these components in longitudinal cross-section. (FIG. 4 shows the turbine carriage 30 in a slightly moved position.) The turbine carriage 30 has an outer diameter slightly smaller than the inner diameter of the handle housing 10, permitting the carriage 30 to move freely (within a limited range of motion) proximally and distally with respect to the handle housing. A control knob 44 is provided to permit the physician to easily move the turbine carriage 30 back and forth. The control knob 44 is connected by a suitable shaft 46 to the turbine carriage 30, the shaft extending outwardly through an elongated slot 12 in the handle housing 10. A collar 48 may be provided around the shaft 46 to reduce friction and guide the shaft along the walls of the slot 12 in the housing. The dimensions of the elongated slot 12 and the collar 48 determine the limits of longitudinal movement of the turbine carriage 30 within the handle housing 10.

The turbine carriage 30 carries a turbine for imparting rotation to the rotatable drive shaft 21. The turbine could be constructed in a variety of suitable ways. In the embodiment depicted in the drawings, the turbine includes a turbine wheel 34 carried on a hollow turbine shaft 36 which passes through a turbine housing 32 containing conventional bearings to support the turbine shaft 36. The hollow turbine shaft 36 in turn is connected to the proximal end of the rotatable drive shaft 21, so that rotation of the turbine wheel 34 by compressed gas imparts rotation to the rotatable drive shaft 21. A set screw 42 (or equivalent mechanical connection) is provided to secure the turbine housing 32 with respect to the turbine carriage 30.

A brake may be provided for preventing the rotation of the turbine wheel 34 and rotatable drive shaft 21 even if compressed gas is supplied to the turbine wheel 34. Although such a brake may be provided in a variety of ways, the preferred embodiment shown in the drawings utilizes a brake shoe 50, carried by the turbine carriage 30 just proximal to the turbine wheel 34, and a brake shoe biasing spring 54 for normally biasing the brake shoe 50 away from the turbine wheel 34. The brake shoe biasing spring 54 is a coil spring disposed between the proximal end of the turbine carriage 30 and a flange 52 extending radially from the brake shoe 50. Other suitable resilient elements may also be employed in place of the coil spring. A set screw 40 (or other suitable mechanism) is provided to prevent the brake shoe 50 from rotating while permitting it to have a limited range of longitudinal movement with respect to the turbine carriage 30 and the turbine wheel 34. This longitudinal movement is needed to permit the brake shoe biasing spring 54 to move the brake shoe 50 away from the turbine wheel 34.

A brake shoe engagement mechanism is also provided for overriding the brake shoe biasing spring 54 and causing the brake shoe 50 to move from a brake shoe-released position, in which position the turbine wheel 34 is free to rotate, to a brake shoe-engaged position, in which position the brake shoe 50 is operatively engaged with the turbine wheel 34 to prevent rotation of the turbine and the drive shaft 21. Preferably the brake shoe engagement mechanism is positioned with respect to the brake shoe 50 so that as the turbine carriage 30 is moved proximally (as is described in more detail below) the brake shoe 50 will encounter the brake shoe engagement mechanism. Further proximal movement of the turbine carriage 30 will then urge the brake shoe 50 against the brake shoe engagement mechanism, compressing the brake shoe biasing spring 54 and moving the brake shoe 50 from its brake shoe-released position to its brake shoe-engaged position. In this position the distal surface of the brake shoe 50 operatively engages the proximal surface of the turbine wheel 34, preventing the turbine wheel 34 from rotating. In FIGS. 3–4 the brake shoe engagement mechanism includes an abutment 80 and a brake shoe engagement spring 78. Both the abutment 80 and the brake shoe engagement spring 78 are carried by an outer telescopic tube 76.

The braking function described above desirably is related to the clamping of the guide wire 20. FIGS. 3–4 depict a type of guide wire clamp that may be used to releasably engage the proximal portion of the guide wire 20 (i.e., that portion of the guide wire 20 that extends proximally from the drive shaft and is seen in the drawings as extending proximally from the turbine) once the distal end of the guide wire 20 has been properly placed across the stenosis and the atherectomy device has been advanced over the guide wire 20. Clamping of the guide wire is desirable to prevent rotation of the guide wire 20 when the turbine and the drive shaft 21 are rotated, and to prevent inadvertent longitudinal movement of the guide wire 20 as the turbine carriage 30 and drive shaft 21 are advanced and retracted.

The basic operation of the guide wire clamp of FIGS. 3–4 is as follows (some specific features of the clamp will be described in more detail below). The clamp is movable from a guide wire-clamped position to a guide wire-released position, and includes a clamp control mechanism (described below) for controlling the position of the clamp. A pair of opposed clamping blocks 92 is provided, each having a clamping surface 93, and a clamp biasing mechanism for biasing at least one of the clamping surfaces 93 toward the other to clamp the guide wire 20. Preferably the clamp biasing mechanism comprises one or more springs for biasing the clamping blocks 92 and their clamping surfaces 93 toward each other to clamp the guide wire 20.

Although any of a variety of springs could be utilized (and some alternate configurations for such springs are described below), in the preferred embodiment, shown in the FIGS. 3–4, a single spring is provided in the form of a resilient circumferential collar 94. In this embodiment, the collar 94 is manufactured to have a substantially round shape. When squeezed into an oval shape and mounted around the clamping blocks 92, the collar 94 attempts to return to its round shape. The size of the clamping blocks 92 preferably is selected so that the combined height of the clamping blocks 92 is slightly greater than the inner diameter of the round collar 94 so that the collar 94, after being placed around the clamping blocks, maintains a slightly oval shape, thus urging the clamping blocks 92 toward each other. Whenever the guide wire 20 is placed between the clamping surfaces 93 of the clamping blocks 92, the clamping blocks 92 are moved radially outwardly slightly, causing the collar 94 to become even more oval in shape, thereby further increasing the pressure on the clamping blocks 92. The oval resilient collar 94 thus exerts pressure on the clamping blocks 92, pinching the guide wire 20 between the clamping surfaces 93 of the clamping blocks 92.

The control knob 44, the turbine carriage 30 and the associated components have three sets of longitudinal positions (or ranges of positions) with respect to the handle housing 10. The significance of these positions (or ranges of positions) is described below:

(1) throughout most of the range of positions of the control knob 44 (see FIGS. 3–4) the clamp is in its guide wire-clamped position, securing the guide wire 20, and the brake is in its brake-released position, permitting the turbine and drive shaft 21 to rotate (this range of positions sometimes will be referred to as the "range of turbine carriage-unlocked positions" or "range of prime mover-unlocked positions", because throughout this range of positions the turbine carriage/prime mover is generally permitted to move freely longitudinally (within a limited range of motion) along the slot 12 in the housing 10);

(2) when the control knob 44 is in the most proximal portion 17 of the slot 12 (see FIG. 5), the clamp is in its guide wire-released position, permitting movement of the guide wire 20, and the brake is in its brake-engaged position, preventing rotation of the turbine and drive shaft 21 (this position sometimes will be referred to as the "turbine carriage-locked position" or "prime mover-locked position" because in the preferred embodiment illustrated in the drawings the turbine carriage/prime mover in this longitudinal position is releasably locked against free movement along the slot 12 in the housing 10); and (3) when the control knob 44 is moved into the narrowed portion 13 of the slot 12, (i.e., when the turbine carriage is moved from the range of turbine carriage-unlocked positions toward the turbine carriage-locked position), the brake becomes engaged, preventing rotation of the turbine and drive shaft 21, while the clamp is not yet released, so movement of the guide wire 20 is not yet possible (this range of positions will be referred to as the range of "transitional positions").

When the control knob 44 is moved from the turbine carriage-unlocked position to the turbine carriage-locked position the brake becomes engaged before the clamp is released. This sequence of operation of the brake and the clamp when the control knob 44 is moved from the turbine carriage-unlocked position to the turbine carriage-locked position assures operational safety of the atherectomy device.

In FIGS. 3–4 the control knob is located within the range of turbine carriage-unlocked positions, with the clamping blocks 92 engaging the guide wire 20 and the brake shoe 50 spaced away from the turbine wheel 34. In the position shown in FIGS. 3–4 compressed gas may be supplied to the turbine wheel 34, causing it, along with the drive shaft 21, to rotate, and permitting the physician to remove stenotic tissue from the lesion being treated. When treating such a stenosis the physician will move the control knob 44 (along with the turbine carriage 30, the turbine and the rotating drive shaft 21) forward and backward, causing the tissue removal section 26 of the drive shaft 21 to advance and retract with respect to the stenosis. The physician typically uses short forward and backward movements of the control knob 44 to remove small portions of the stenotic tissue with each stroke. Typically many such strokes are required to completely cross a stenotic lesion, and often more than one lesion must be treated along a length of an artery. Thus, desirably the tissue removal section 26 is capable of being moved longitudinally through a range of positions to permit treatment of more than one lesion without having to reposition the catheter 22 within the artery.

The total range of longitudinal movement of the drive shaft 21 (and its tissue removal section 26) with respect to the catheter 22 is determined by the length and configuration of the slot 12 in the handle housing 10. The limit on forward (distal) movement of the drive shaft 21 with respect to the catheter 22 (i.e., the distal end of the range of turbine carriage-unlocked positions) is reached when the control knob 44 is moved distally and the collar 48 encounters the distal end of the slot 12. The proximal end of the range of turbine carriage-unlocked positions of the drive shaft 21 with respect to the catheter 22 is reached when the control knob 44 is moved proximally and the collar 48 encounters a narrowed portion 13 of the slot 12 in the handle housing 10. Throughout the range of turbine carriage-unlocked positions the brake is in its brake-released position, permitting the turbine and drive shaft 21 to rotate, and the clamp is in its guide wire-clamped position, preventing the guide wire 20 from moving.

In order to advance the drive shaft 21 and the handle of the atherectomy device over the guide wire 20 or to remove the guide wire from the atherectomy device the control knob 44 is moved from the range of turbine carriage-unlocked positions through the range of transitional positions into the turbine carriage-locked position. This is accomplished by applying a little extra rearward force on the control knob 44 to urge the collar 48 in between the walls of the narrowed portion 13 of the slot 12. A relief slot 14 is provided proximally of the main elongated slot 12, permitting the opposing walls of the narrowed portion 13 of the slot 12 to move slightly away from each other, thus slightly expanding the diameter and circumference of this portion of the handle housing 10 to permit the collar 48 to pass through the narrowed portion 13 of the slot 12. Desirably the handle housing is made from a somewhat resilient material (preferably a suitable plastic such as ABS) to permit it to radially expand slightly and act as a type of spring, regaining its original diameter and circumference when the control knob 44 is moved out of the range of transitional positions.

The preferred embodiment illustrated in the drawings utilizes the resilient nature of the handle housing 10 and a narrowed portion 13 of the slot 12 as a type of detent to prevent the control knob 44 from entering the range of transitional positions without the exertion of a little extra force, thereby preventing inadvertent movement of the control knob 44 from the range of turbine carriage-locked positions into the turbine carriage-unlocked position, and vice versa. Other types of mechanical restrictions in the slot 12 may also be provided to serve this function, such as a spring biased detent mechanism, or equivalent structures. Thus, this disengagable mechanical linkage functions as a turbine carriage lock for automatically restraining the turbine carriage 30 from longitudinal movement with respect to the handle when the turbine carriage 30 is moved longitudinally to the turbine carriage-locked position. (The "turbine carriage lock" is sometimes referred to as the "prime mover lock" for automatically restraining the prime mover from longitudinal movement with respect to the handle when the prime mover is moved longitudinally to the prime mover-locked position.) Other types of disengagable mechanical linkages between the turbine carriage and the handle may also be utilized to function as a turbine carriage lock for releasably locking the turbine carriage in the turbine carriage-locked position. Many types of such linkages will include a pair of interlocking members that are releasably engageable with each other, one of the members being carried by the turbine carriage 30 and the other being carried by the handle. Such interlocking members may be comprised of a detent and complementary member engageable with the detent, such as the narrowed portion 13 (detent) of the slot 12 and the collar 48 (complementary member) discussed above.

When the control knob 44 is being moved through the range of transitional positions the brake pad 62 carried by the brake shoe 50 engages the proximal surface of the turbine wheel 34 to prevent the rotation of the turbine wheel 34 and the attached drive shaft 21. This braking of the turbine wheel 34 occurs while the clamping blocks 92 are still firmly gripping the guide wire 20. Further proximal movement of the control knob 44 will move the control knob 44 out of the range of transitional positions and into the turbine carriage-locked position shown in FIG. 5–6. In the turbine carriage-locked position, the clamping blocks 92 are spaced from each other to release the guide wire 20, and the turbine wheel 34 continues to be firmly engaged by the brake shoe 50 to prevent rotation of the turbine and drive shaft 21. The collar 48 no longer engages the walls of the narrowed portion 13 of the slot 12 in the handle housing 10, but rather is located in the most proximal portion 17 of the slot 12. The control knob 44 and the turbine are thus "locked" in the turbine carriage-locked position by the narrowed portion 13 of the slot 12. The control knob 44 and the turbine may be moved out of this turbine carriage-locked position by applying a little extra forward force to the control knob 44 to urge the collar 48 in between the walls of the narrowed portion 13 of the slot 12, through the range of transitional positions and into the range of turbine carriage-unlocked positions, where the control knob 44 and the turbine are free to be moved along the range of turbine carriage-unlocked positions.

The mechanism for causing the braking and unclamping sequence that occurs as the control knob 44 is moved from the range of turbine carriage-unlocked positions through the range of transitional positions to the turbine carriage-locked position is as follows. Referring again to FIGS. 3–4 (which show the control knob 44 in the range of turbine carriage-unlocked positions), the brake shoe engagement mechanism is located proximally of the brake shoe 50. As described above, the brake shoe engagement mechanism includes an abutment 80 and a brake shoe engagement spring 78. Both the abutment 80 and the brake shoe engagement spring 78 are carried by an outer telescopic tube 76. The outer telescopic tube 76 is carried by a housing 90 of the guide wire clamp with the proximal end of the outer telescopic tube 76 extending into the central opening of the clamp housing 90. Thus, the brake shoe engagement spring 78 is compressed between the abutment 80 and the clamp housing 90. The brake shoe engagement spring 78 may be a conventional coil spring as is shown in FIGS. 3–4 (the diameter and pitch of the brake shoe engagement spring 78 are somewhat exaggerated in the drawings for the sake of clarity—preferably the inner diameter of the brake shoe engagement spring 78 is just slightly larger than the outer diameter of the outer telescopic tube 76). The abutment 80 in this embodiment is comprised of a tube with an inner diameter that is larger than the outer diameter of the outer telescopic tube 76. The abutment tube 80 is interlocked with the outer telescopic tube 76 by an inner collar 86 and an outer collar 89. The inner collar 86 is secured to the inner surface of the abutment tube 80, and the outer collar 89 is secured to the distal end of the outer telescopic tube 76. This interlocking configuration, formed by the inner collar 86 and the outer collar 89, prevents the brake shoe engagement spring 78 from pushing the proximal end of the abutment tube 80 distally beyond the distal end of the outer telescopic tube 76.

When the control knob 44 is located in the range of turbine carriage-unlocked positions, as it is in FIGS. 3–4, the distal end of the abutment 80 is spaced from the proximal surface of the brake shoe 50, and the brake shoe biasing spring 54 prevents the brake shoe 50 from contacting the turbine wheel 34. When the control knob 44 is moved to the proximal end of the range of turbine carriage-unlocked positions, the proximal surface of the brake shoe 50 contacts the distal end of the abutment 80, but the brake shoe 50 has not yet operatively engaged the turbine wheel 34. As the control knob 44 is moved further proximally into the range of transitional positions, the distal end of the abutment 80 begins to press against the proximal surface of the brake shoe 50. The brake shoe engagement spring 78 is designed and selected to be sufficiently strong that it overpowers the brake shoe biasing spring 54, urging the brake shoe 50 against the turbine wheel 34. Engagement of the brake shoe 50 with the turbine wheel 34 prevents rotation of the turbine wheel 34.

As the control knob 44 is moved through the range of transitional positions and the braking of the turbine wheel 34 is occurring, another movement is also in progress to release the clamp. FIGS. 3–4, which show the control knob 44 in the range of turbine carriage-unlocked positions, also depict the clamp control mechanism which provides control of the position of the clamp, the clamp being movable from a guide wire-clamped position to a guide wire-released position. Preferably the clamp control mechanism comprises a clamp control rod having a proximal end portion and a distal end portion, the distal end portion of the clamp control rod being operatively connected to the brake shoe 50. In FIGS. 3–4 the clamp control rod is actually a tube (clamp control tube 70), having a central lumen through which the guide wire 20 may pass.

The clamp control tube 70 is slidably received within a central lumen of the outer telescopic tube 76. The clamp control tube 70 is longer than the outer telescopic tube 76, and is longitudinally movable with respect to the guide wire clamp from a range of clamp-released positions (sometimes referred to as a "range of disengaged positions") to a clamp-engaged position (sometimes referred to as an "engaged position"), in which position the proximal end portion of the clamp control tube 70 extends proximally beyond the proximal end of the outer telescopic tube 76 and becomes wedged between the clamping blocks 92, thereby releasing the guide wire 20 from the clamp.

Figure 5:
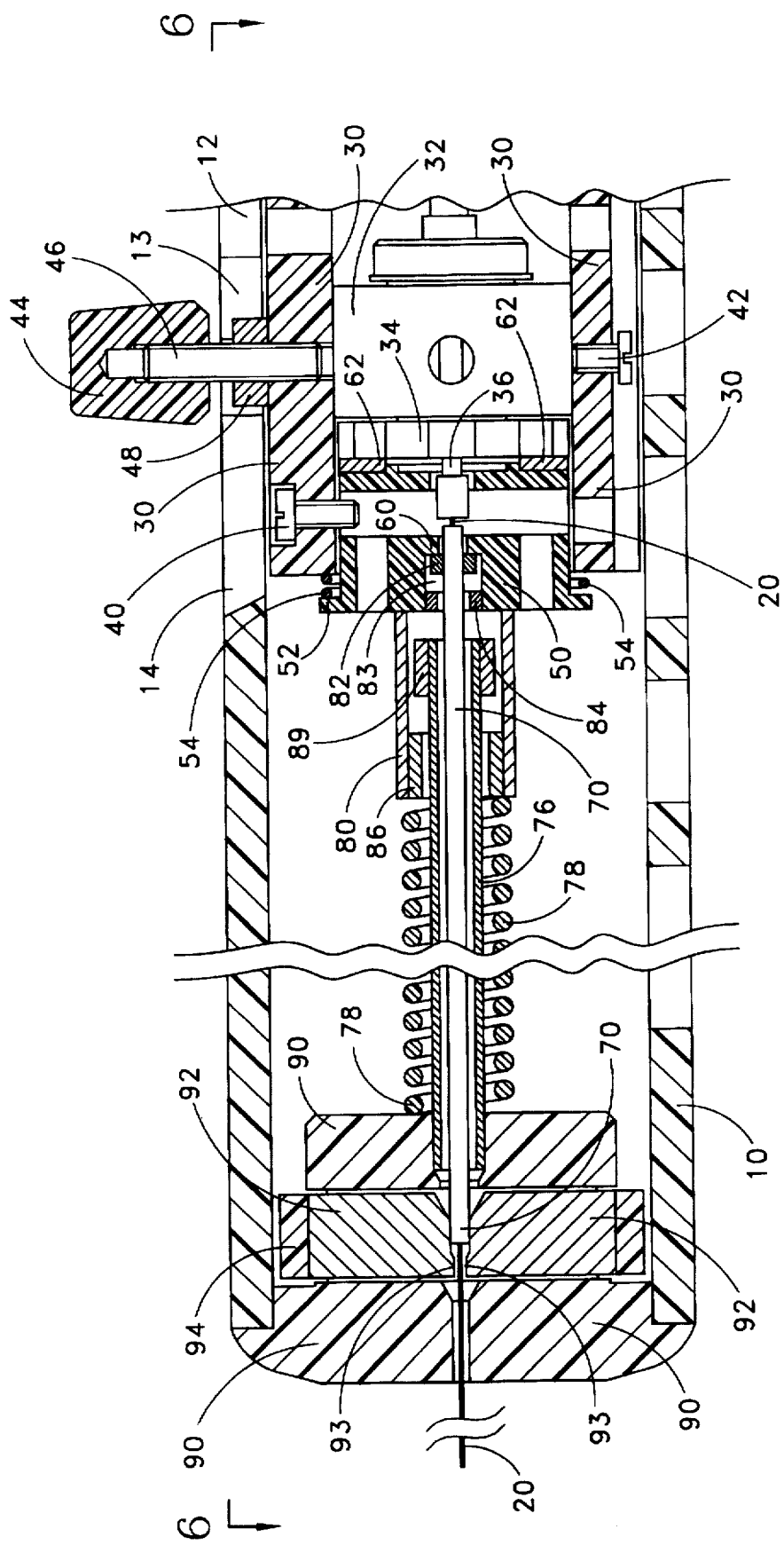
FIG. 5 is a longitudinal cross-sectional view similar to FIG. 4, showing the atherectomy device in another moved position, the turbine carriage being located in its turbine carriage-locked position.
Figure 6:
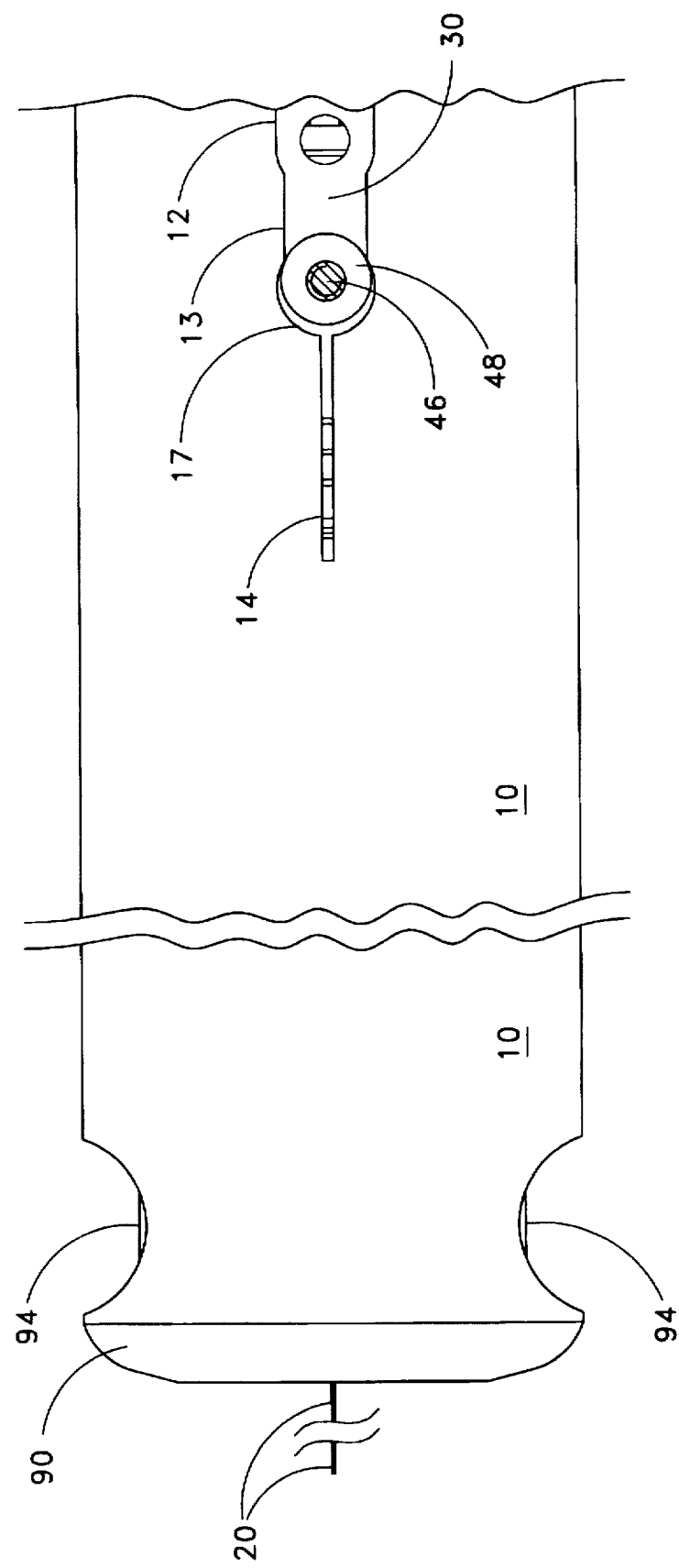
FIG. 6 is a top view (partial cross-section haven been taken along lines 6—6 of FIG. 5) showing the proximal portion of the atherectomy device in the position illustrated in FIG. 5.

The clamp control tube 70 includes a radially outwardly extending flange 82 (here shown as a separate component secured to a distal end portion of the clamp control tube 70), the brake shoe including a central cavity 83 capturing the radially outwardly extending flange 82. Longitudinal movement of the flange 82 is restricted distally by shoulder 60 of the brake shoe 50 and proximally by a complementary flange 84 secured to the brake shoe 50. Thus, the clamp control tube 70 generally moves forward and backward together with the brake shoe 50 as the brake shoe 50 is moved forward and backward together with the turbine carriage 30 in response to the forward and backward movements of the control knob 44. When the control knob 44 is located in the range of turbine carriage-unlocked positions, as shown in FIGS. 3–4, the proximal end of the clamp control tube 70 is spaced quite a distance from the clamping blocks 92. In FIG. 5 the control knob 44 has been moved completely through the range of transitional positions to its most proximal position, the turbine carriage-locked position. In this position, the brake continues to be engaged while the proximal end portion of the clamp control tube 70, acting as a wedge, has been urged between the clamping blocks 92, spacing the clamping surfaces 93 from each other and moving the guide wire clamp into its guide wire-released position. When the control knob 44 has been moved into the turbine-locked position and the guide wire clamp has been moved into its guide wire-released position, both the drive shaft 21 and the handle of the atherectomy device may be advanced over the guide wire 20 (at the beginning of the procedure), the guide wire 20 may be repositioned (during the atherectomy procedure), or the guide wire 20 may be removed from the device (at the end of the procedure). When the control knob 44 is moved into the turbine-locked position the brake becomes automatically engaged with the turbine well before the clamp is released; thus there is no opportunity for the turbine and drive shaft 21 to rotate when the guide wire 20 is unclamped. Braking the turbine wheel 34 in the turbine-locked position assures operational safety of the device because the turbine will not rotate in the turbine carriage-locked position even if compressed gas is supplied to the turbine.

FIGS. 7-11 depict details of the structure and function of a preferred guide wire clamp. In addition to releasing the guide wire 20 from the clamp each time when the turbine carriage and the turbine are placed in the prime mover-locked position, this clamp also enables the operator to release the guide wire 20 from the clamp even when the clamp control mechanism is in the guide wire-clamped position. A pair of opposed clamping blocks 92 is disposed in a slot 91 in the clamp housing 90. A clamp biasing mechanism, comprised of at least one clamp biasing spring, is provided for biasing at least one of the clamping blocks 92 toward the other to clamp the guide wire 20. Each of the clamping blocks 92 includes a clamping surface 93 and a spring engaging surface 131. The clamp biasing spring preferably comprises a resilient collar 94 encircling the clamping blocks 92, the size and shape of the clamping blocks 92 and the resilient collar 94 being selected so that the resilient collar 94 pushes on the spring engaging surfaces 131 to bias the clamping blocks 92 toward each other, clamping the guide wire 20 between the clamping surfaces 93.

The handle housing 10 is sized and shaped with respect to the collar 94 to permit manual compression of the collar 94. Preferably the handle housing 10 substantially surrounds the collar 94, the handle housing 10 including at least one clamp override opening 18 (and preferably two such openings 18) aligned with the collar 94 to permit manual compression of the collar 94. Thus, the resilient circumferential collar 94 may be manually compressed (through the openings 18 in the handle housing 10) to a shape in which the collar 94 does not bias the clamping blocks 92 toward each other and the guide wire 20 is released from the clamp.

As is illustrated in FIG. 8A, the clamping surfaces 93 of the clamping blocks 92 may be provided with a coating of diamond chips 102, secured by a suitable bonding material 103, to provide a better grip on the guide wire 20. Other equivalent techniques may be utilized to provide adequate engagement of the clamping surfaces 93 with the guide wire 20.

Figure 9:
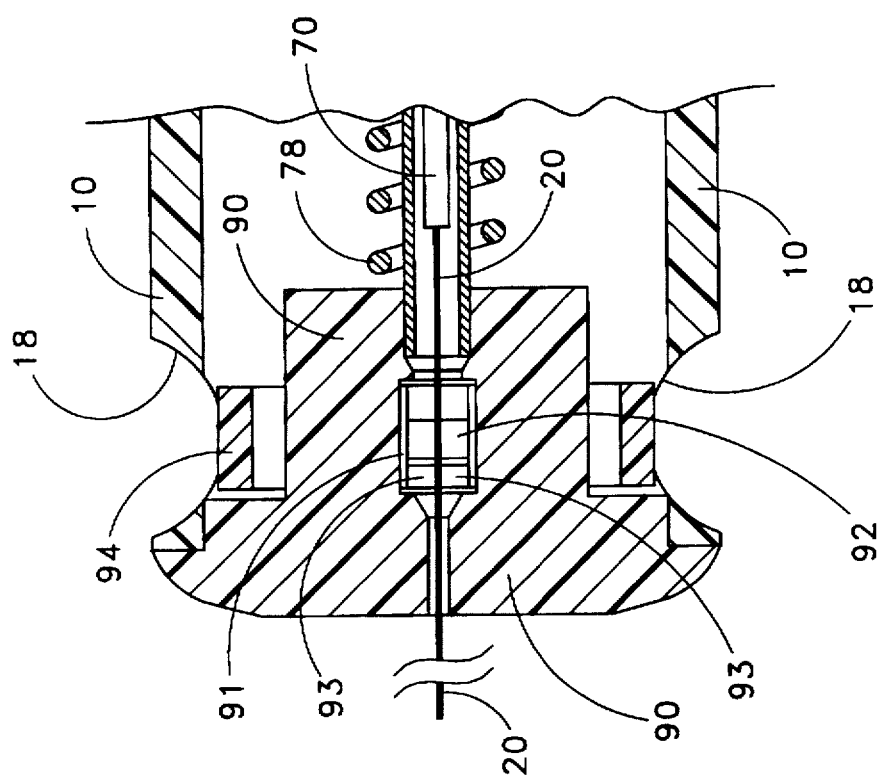
FIG. 9 is a longitudinal cross-sectional view of FIG. 7, taken along lines 9—9 thereof.

FIG. 9 is a cross-sectional view of the clamp taken along lines 9—9 of FIG. 7. This view shows additional details of the clamp housing 90 which contains the clamping blocks 92, and also illustrates the alignment of a pair of clamp override openings 18 in the handle housing 10 with the resilient circumferential collar 94.

Figure 11:
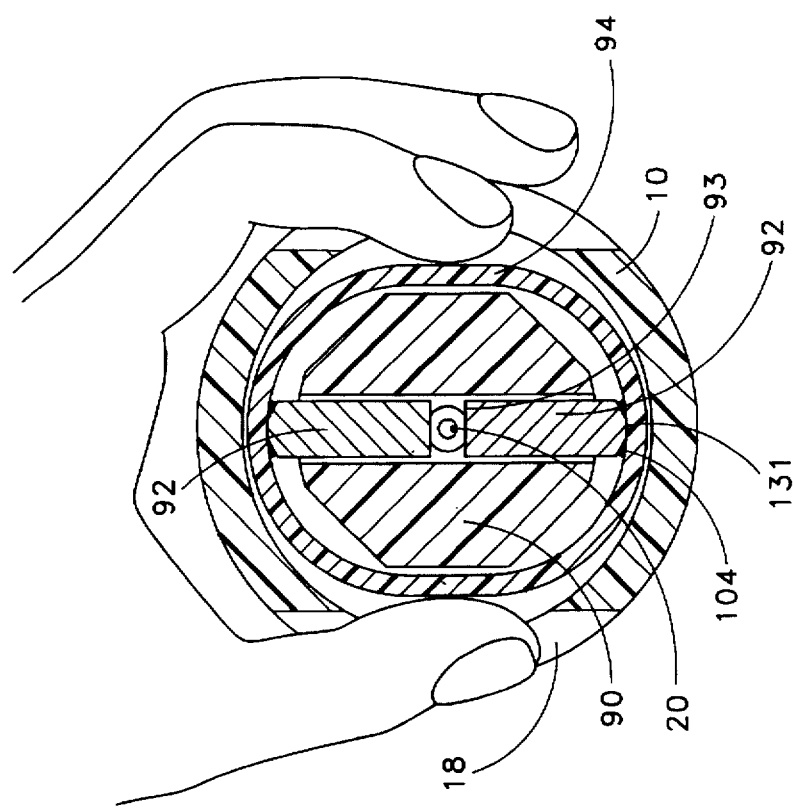
FIG. 11 is a transverse cross-sectional view of the clamp portion of the atherectomy device of FIG. 10, shown in a moved position.
Figure 10:
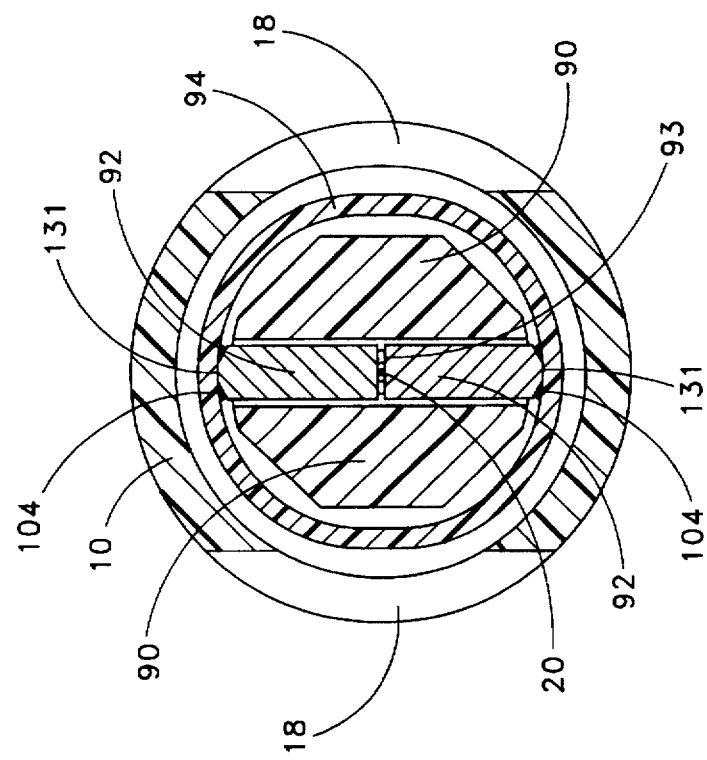
FIG. 10 is a transverse cross-sectional view of the clamp portion of an atherectomy device of the invention.

In FIG. 10 the guide wire 20 is clamped between the clamping surfaces 93 of the clamping blocks 92. As may been seen by comparing the shape of the resilient collar 94 in FIGS. 10 and 11, the clamp override openings 18 permit manual compression of the collar 94 to a shape in which the deformed collar 94 does not bias the clamping blocks 92 toward each other and in which the guide wire 20 is released from the clamp even if the clamp control mechanism is in the guide wire-clamped position. In FIG. 11 the clamping blocks are depicted as being spaced away from the guide wire-in this embodiment of the clamp each clamping block 92 is secured (such as by an adhesive 104) to the resilient collar 94 so that when the collar 94 is compressed it actually pulls the clamping blocks 92 away from the guide wire 20. The use of such an adhesive 104 is not necessarily required, however.

As described above, in certain circumstances it is desirable to permit the user to release the guide wire clamp even when the drive shaft 21 is rotating. It is for this purpose that the handle housing 10 includes at least one clamp override opening 18 (and preferably two openings 18) aligned with the collar 94 to permit manual compression of the collar 94 to release the guide wire 20 from the clamp. Under some circumstances, however, an operator may wish to hold the guide wire clamp in the guide wire-released position for more than just a few moments, such as when advancing or retracting the drive shaft 21 over the guide wire 20 with the drive shaft being rotated at relatively low speeds (e.g., about 50,000 rpm to about 90,000 rpm)—this technique is described in greater detail above in the background section. To facilitate use of this technique, the invention provides an override clamp 140 which is removably securable to the handle housing 10 to move the guide wire clamp to its guide wire-released position and to hold the guide wire clamp in such position as long as the override clamp 140 is secured to the handle housing. Thus, the override clamp 140 allows the guide wire clamp to be moved to its guide wire-released position safely and reliably without continuously occupying one of the operator's hands (or one of the assistant's hands).

A suitable override clamp can be constructed to have a variety of configurations depending on the size and shape of the handle housing 10 and the number and location of the clamp override openings 18. FIG. 2 illustrates a preferred configuration for an override clamp 140 used on a generally cylindrical handle housing 10 having two clamp override openings. The override clamp 140 has a generally C-shaped clamp portion 143 which includes a pair of inwardly protruding curved buttons 145 for operative engagement with the clamp biasing mechanism (i.e., in the embodiment shown in FIG. 2, the resilient collar 94). Each of the buttons 145 is generally hemispherical in shape, though other suitable shapes may also be used. The clamp override openings 18 in the handle housing 10 and the C-shaped portion 143 of the override clamp 140 are sized, shaped and positioned so that the buttons 145 align with the clamp override openings 18, permitting the override clamp 140 to compress the resilient collar 94 to move the guide wire clamp to its guide wire-released position. Preferably each curved button 145 protrudes into its respective override opening 18 sufficiently that the generally C-shaped portion 143 of the override clamp 140 becomes removably interlocked with the handle housing 10. Preferably the override clamp 140 also includes opposing ends which include outwardly extending ears 147 to facilitate removal of the override clamp 140 from the handle housing 10.

In the embodiment illustrated in FIG. 2 the override clamp 140 of the invention is used with an atherectomy device that has a prime mover connected to a control knob 44. FIGS. 3-6 show that the prime mover is connected to the control knob 44 by a shaft 46 which extends outwardly through a longitudinal slot 12 in the handle housing 10. The control knob 44 facilitates longitudinal movement of the prime mover and drive shaft 21 with respect to the handle housing 10. In the preferred embodiment it is possible to use the override clamp 140 not only to move the guide wire clamp into its guide-wire released position, but also to lock the control knob 44 in a particular longitudinal position with respect to the handle housing 10. This may be achieved by providing the override clamp 140 with a mechanical linkage engagable with the control knob 44 to prevent longitudinal movement of the control knob 44 (and, consequently, the prime mover together with the drive shaft 21 and its tissue removal implement 26). Preferably the mechanical linkage comprises a distally extending strap 141 having an orifice 142 sized to closely receive and retain the control knob 44 therein. In FIG. 2 the orifice is shown as being located at the distal end of the strap 141.

Figure 12:
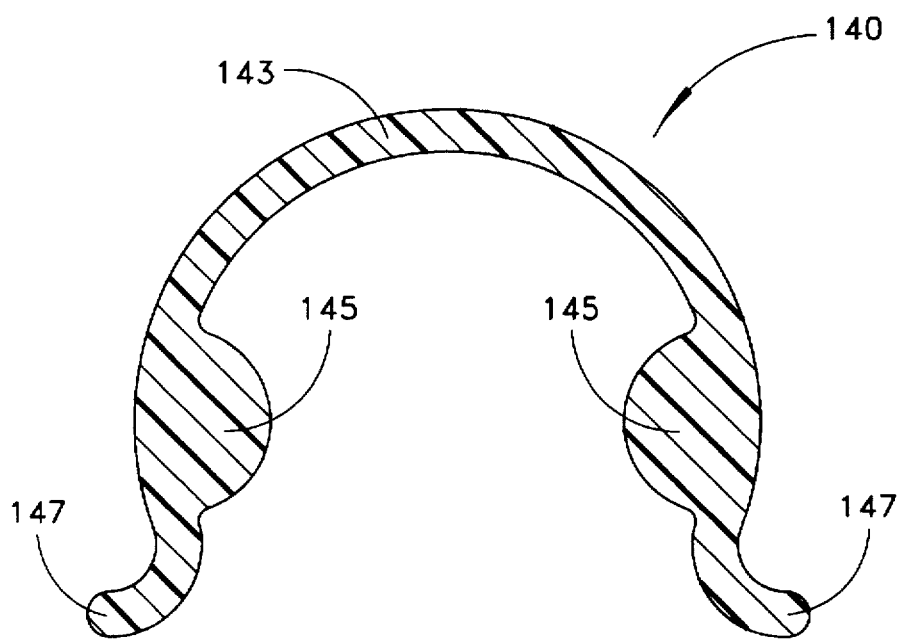
FIG. 12 is a transverse cross-sectional view of the override clamp depicted in FIG. 2, taken along lines 12—12 thereof.
Figure 13:
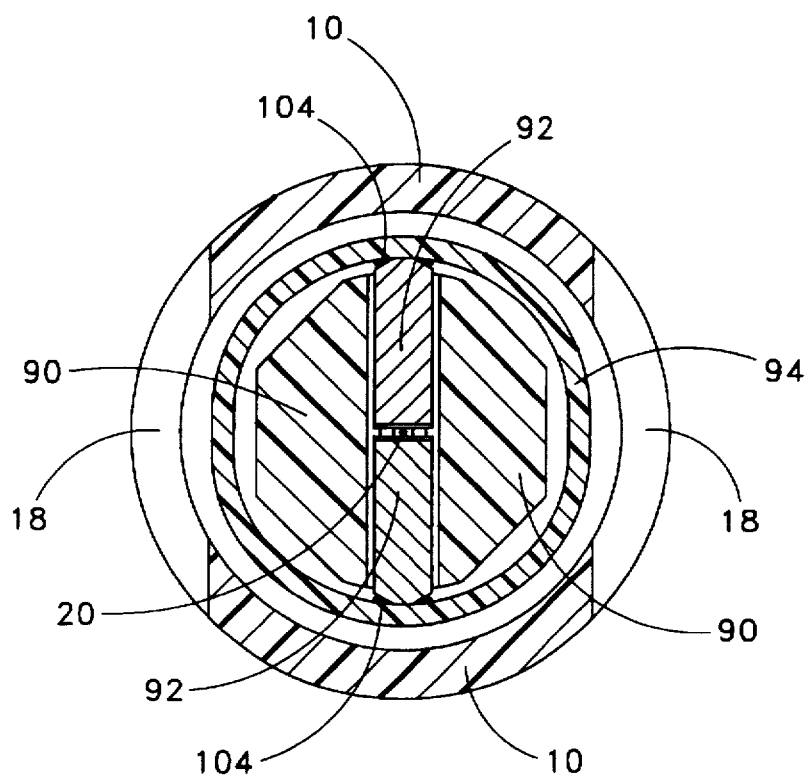
FIG. 13 is a transverse cross-sectional view of the clamp portion of the atherectomy device depicted in FIG. 2, taken along lines 13—13 thereof.
Figure 14:
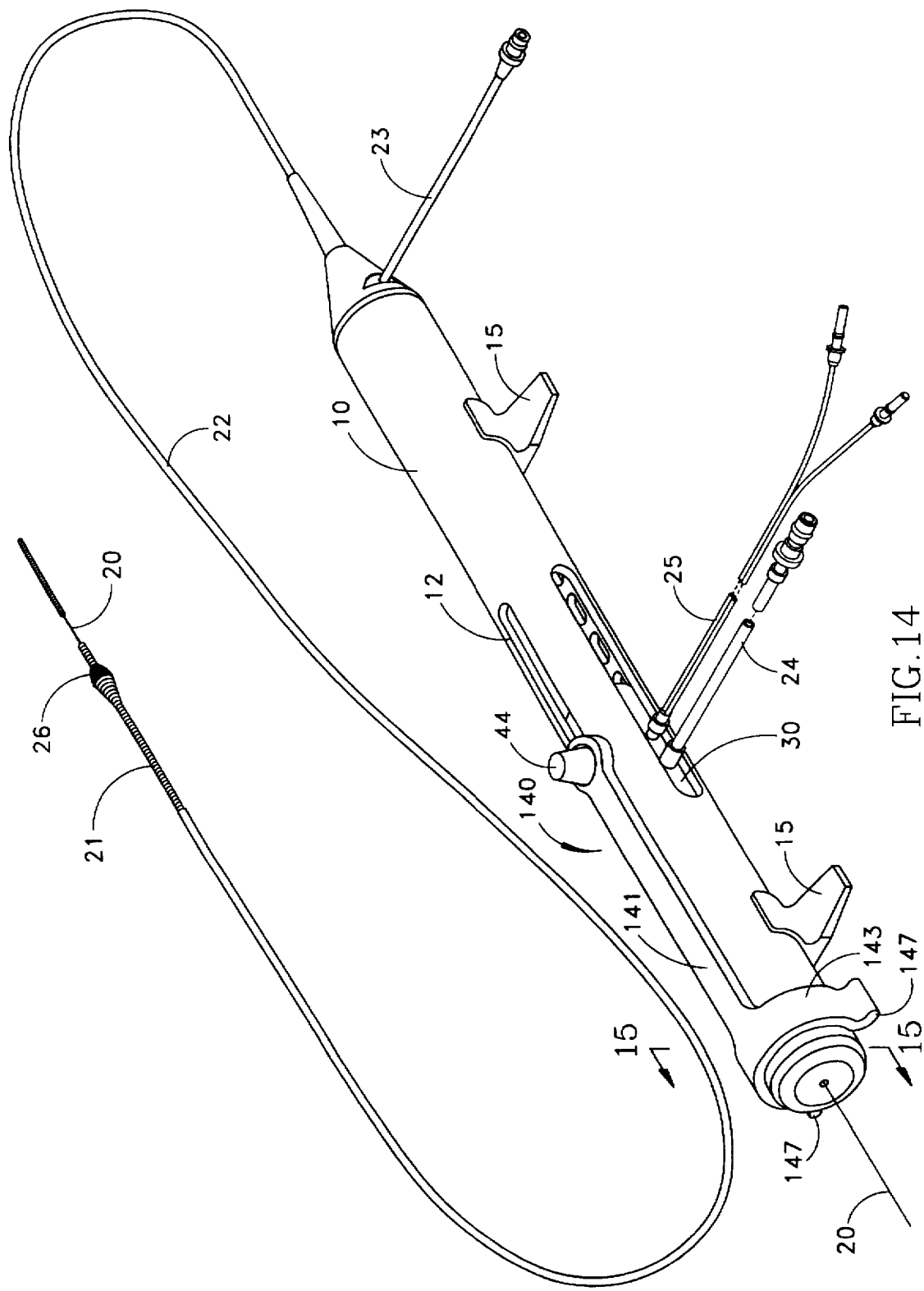
FIG. 14 is a perspective view of the rotational atherectomy device depicted in FIG. 2 with the override clamp secured to the handle housing.
Figure 15:
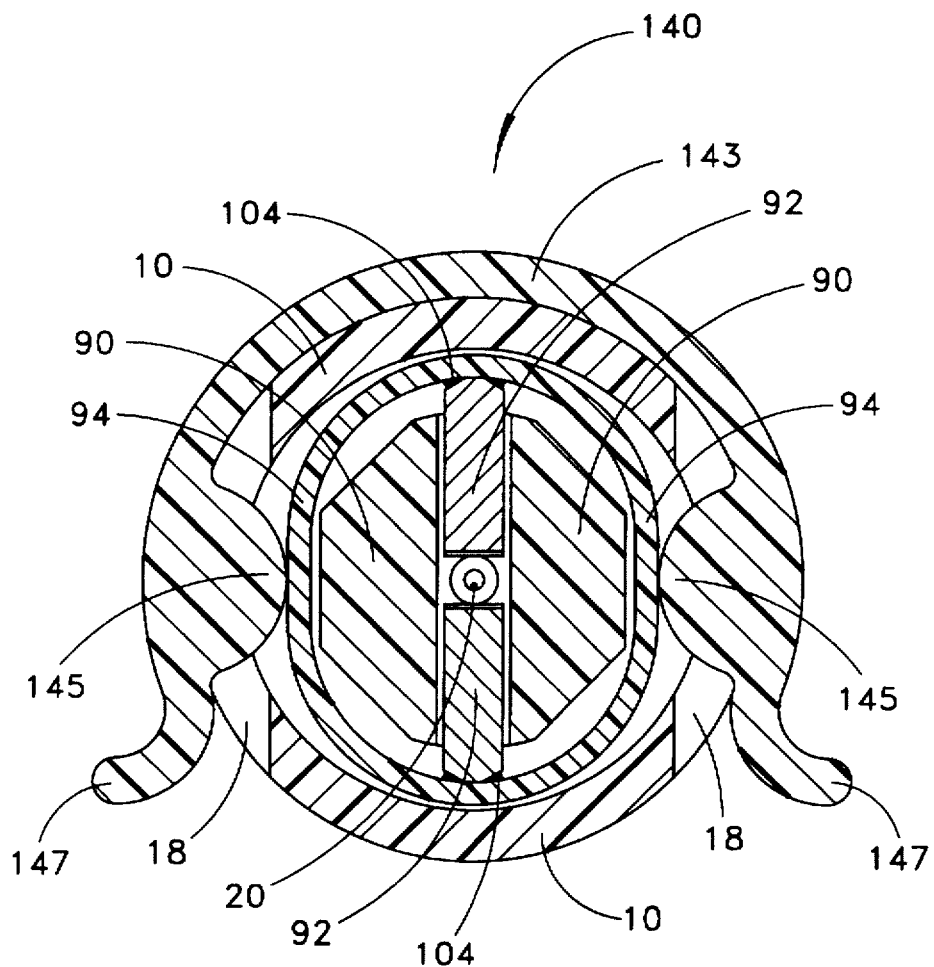
FIG. 15 is a transverse cross-sectional view of FIG. 14, taken along lines 15—15 thereof.

FIG. 12 illustrates in transverse cross-section the generally C-shaped portion 143 of the override clamp 140, and FIG. 13 illustrates in transverse cross-section the portion of the handle housing 10 onto which the override clamp 140 may be snapped. FIG. 14 depicts in perspective view the atherectomy device with the override clamp 140 snapped onto the handle housing 10, thereby releasing the guide wire from the guide wire clamp and locking the control knob 44, together with the prime mover carriage and the prime mover, in a specific longitudinal position with respect to the handle housing 10. FIG. 15 shows in transverse cross-section the interaction of the override clamp 140 of the invention with the resilient collar 94 of the guide wire clamp. The resilient collar 94 has been compressed by the curved buttons 145 of the override clamp 140 to a shape in which the deformed collar 94 no longer biases the clamping blocks toward each other, thereby releasing the guide wire 20 from the guide wire clamp. The configuration of the guide wire clamp in FIG. 15 is essentially the same as that in FIG. 11. The only difference between FIG. 15 and FIG. 11 is that the resilient collar 94 has been compressed by the override clamp 140 in FIG. 15 rather than by the fingers of the operator in FIG. 11. FIGS. 16 and 17 illustrate details of the override clamp 140 of the invention in transverse and longitudinal cross-section, respectively.

As indicated above, the override clamp of the invention may be constructed in a wide variety of suitable configurations. FIG. 18 illustrates just one other possibility. While the override clamp of FIGS. 2 and 12-17 may be molded conveniently from suitable plastics, the override clamp 140' of FIG. 18 may be stamped out of a suitable metal such as any of a variety of spring steels. This clamp 140' also has a generally C-shaped portion 143' with a pair of inwardly protruding curved buttons 145' for operative engagement with the clamp biasing mechanism, and opposing ends which include outwardly extending ears 147' to facilitate removal of the override clamp 140' from the handle housing 10.

While a preferred embodiment of the present invention has been described, it should be understood that various changes, adaptations and modifications may be made therein without departing from the spirit of the invention and the scope of the appended claims.

What is claimed is:

1. An atherectomy device comprising:

a handle housing;

a rotatable prime mover movable longitudinally with respect to the handle housing;

a rotatable drive shaft having a proximal end connected to the prime mover for rotation and longitudinal movement therewith, and a distal end portion having a tissue removal implement usable to remove tissue from a bodily passageway;

a guide wire disposed within the drive shaft and having a proximal portion extending proximally from the proximal end of the drive shaft;

a guide wire clamp disposed within the handle housing for releasably clamping the proximal portion of the guide wire, the guide wire clamp being selectively movable from a guide wire-clamped position to a guide wire-released position;

the handle housing being shaped and sized with respect to the guide wire clamp to permit manual movement of the guide wire clamp from its guide wire-clamped position to its guide wire-released position; and an override clamp removably securable to the handle housing to move the guide wire clamp to the guide wire-released position and to hold the guide wire clamp in such position.

2. The atherectomy device of claim 1 wherein the handle housing substantially surrounds the guide wire clamp, the handle housing including one or more clamp override openings aligned with the guide wire clamp to permit manual manipulation of the guide wire clamp.

3. The atherectomy device of claim 2 wherein the guide wire clamp is comprised of a pair of opposed clamping blocks, each having a clamping surface, and a resilient collar encircling the clamping blocks, the size and shape of the clamping blocks and the resilient collar being selected so that the resilient collar biases the clamping surfaces toward each other to clamp the guide wire.

4. The atherectomy device of claim 3 wherein the handle housing includes two clamp override openings aligned with the resilient collar, thereby permitting the override clamp to compress the resilient collar to move the guide wire clamp to its guide wire-released position.

5. The atherectomy device of claim 4 wherein the prime mover is located within the handle housing, the handle housing having a longitudinal slot through which the prime mover is connected to a control knob external to the handle housing, the override clamp including a mechanical linkage engagable with the control knob to prevent longitudinal movement of the control knob and the prime mover with respect to the handle housing.

6. The atherectomy device of claim 5 wherein the mechanical linkage comprises a distally extending strap having an orifice sized to closely receive and retain the control knob therein.

7. The atherectomy device of claim 4 wherein the override clamp includes a generally C-shaped portion.

8. The atherectomy device of claim 7 wherein the generally C-shaped portion of the override clamp includes an inwardly protruding curved button for operative engagement with the resilient collar.

9. The atherectomy device of claim 8 wherein the button is generally hemispherical in shape.

10. The atherectomy device of claim 7 wherein the handle housing has a pair of generally opposing clamp override openings and wherein the C-shaped portion of the override clamp also includes a pair of generally opposing inwardly protruding curved buttons for operative engagement with the resilient collar.

11. The atherectomy device of claim 10 wherein, when the override clamp is positioned on the handle housing, each curved button of the override clamp protrudes into its respective override opening sufficiently that the generally C-shaped portion of the override clamp becomes removably interlocked with the handle housing.

12. The atherectomy device of claim 7 wherein the generally C-shaped portion of the override clamp includes opposing ends which include outwardly extending ears to facilitate removal of the override clamp from the handle housing.

13. An atherectomy device comprising:

a handle housing;

a rotatable prime mover disposed within the handle housing and being movable longitudinally with respect to the handle housing;

a rotatable drive shaft having a proximal end connected to the prime mover for rotation and longitudinal movement therewith, and a distal end portion having a tissue removal implement usable to remove tissue from a bodily passageway;

a guide wire disposed within the drive shaft and having a proximal portion extending proximally from the proximal end of the drive shaft;

a guide wire clamp disposed within the handle housing and comprised of a pair of opposed clamping blocks and a clamp biasing mechanism for moving the clamping blocks from a guide wire-released position to a guide wire-clamped position;

the handle housing including one or more clamp override openings aligned with the clamp to permit manual override of the clamp biasing mechanism; and an override clamp removably securable to the handle housing in alignment with the one or more clamp override openings and causing the clamp biasing mechanism to release the clamping blocks from the guide wire-clamped position.

14. The atherectomy device of claim 13 wherein the handle housing has a longitudinal slot through which the prime mover is connected to a control knob external to the handle housing, the override clamp including a mechanical linkage engagable with the control knob to prevent longitudinal movement of the control knob and the prime mover with respect to the handle housing.

15. The atherectomy device of claim 14 wherein the mechanical linkage comprises a distally extending strap having an orifice sized to closely receive and retain the control knob therein.

16. The atherectomy device of claim 13 wherein the override clamp includes a generally C-shaped portion.

17. The atherectomy device of claim 16 wherein the generally C-shaped portion of the override clamp includes an inwardly protruding curved button for operative engagement with the clamp biasing mechanism.

18. The atherectomy device of claim 17 wherein the button is generally hemispherical in shape.

19. The atherectomy device of claim 16 wherein the handle housing has a pair of generally opposing clamp override openings and wherein the C-shaped portion of the override clamp also includes a pair of generally opposing inwardly protruding curved buttons for operative engagement with the clamp biasing mechanism.

20. The atherectomy device of claim 19 wherein, when the override clamp is positioned on the handle housing, each curved button of the override clamp protrudes into its respective override opening sufficiently that the generally C-shaped portion of the override clamp becomes removably interlocked with the handle housing.

21. The atherectomy device of claim 16 wherein the generally C-shaped portion of the override clamp includes opposing ends which include outwardly extending ears to facilitate removal of the override clamp from the handle housing.

22. An atherectomy device comprising:

a handle housing;

a rotatable drive shaft having a proximal end and a distal end portion with a tissue removal implement usable to remove tissue from a bodily passageway;

a guide wire disposed within the drive shaft and having a proximal portion extending proximally from the proximal end of the drive shaft;

a guide wire clamp carried by the handle housing for releasably clamping the proximal portion of the guide wire, the guide wire clamp being selectively movable from a guide wire-clamped position to a guide wire-released position; and an override clamp removably securable with respect to the handle housing to move the guide wire clamp to the guide wire-released position and to hold the guide wire clamp in such position.

* * * * *